United States Patent [19]

Harle

[11] Patent Number: 4,610,664
[45] Date of Patent: Sep. 9, 1986

[54] OPERATION ASPIRATOR WITH CONTROL VALVE

[76] Inventor: Anton Harle, Drechslerweg 40, Munster, Fed. Rep. of Germany

[21] Appl. No.: 639,076

[22] Filed: Aug. 9, 1984

[51] Int. Cl.[4] .............................................. A61M 1/00
[52] U.S. Cl. ..................................... 604/119; 604/34; 604/902; 251/9; 433/95
[58] Field of Search ................ 604/34, 119, 902, 245, 604/118; 137/8; 251/9, 331, 342; 433/95

[56] References Cited

U.S. PATENT DOCUMENTS 4,504,266  3/1985  Härle .................................. 251/303

FOREIGN PATENT DOCUMENTS 1491755 12/1966 Fed. Rep. of Germany .
1566561  2/1967 Fed. Rep. of Germany .
2950323  4/1981 Fed. Rep. of Germany .
1537204  5/1967 France .

Primary Examiner—C. Fred Rosenbaum
Assistant Examiner—J. L. Kruter
Attorney, Agent, or Firm—Merchant, Gould, Smith, Edell, Welter & Schmidt

[57] ABSTRACT

The application discloses an operation aspirator with which, without provoking contamination of the aspirator opening, fine-metering of the vacuum that is available at the aspirator opening is possible and actuation of the valve apparatus closing off the suctioning line is simultaneously made easier.

7 Claims, 5 Drawing Figures

OPERATION ASPIRATOR WITH CONTROL VALVE

FIELD OF THE INVENTION

The invention concerns an operation aspirator for suctioning out liquids, during surgical interventions, with a suctioning tube capable of being guided manually into the field of operation and with a check valve-like interrupting member for the suctioning stream, with the check valve-like interrupting member capable of being operated by the hand holding the suctioning tube, and a valve stem capable of being brought into its working position against the action of an elastic reset force and that displays a passthrough opening that is to be brought in to alignment with the suctioning tube.

BACKGROUND OF THE INVENTION

Described in DE-AS 29 50 323, which shows a species type apparatus of the type described above, is an operation aspirator wherein the suctioning tube consists of two pieces of tubing assembled over a housing, and the one tubing end, preferentially cut off diagonally,, forms a seat in the housing for the valve flap that is capable of being lifted from the seat by means of a pin penetrating the housing wall at an elastic spot. Contaminating of the aspirator tube opening by the operating person is herewith avoided. The manner in which the flexible supporting of the valve flap is arranged is technically difficult for manufacturing and the force for lifting the valve flap is relatively high, so that the hand of the operator handling the aspirator is strongly encumbered.

With a closed valve flap, the vacuum prevailing in the suctioning tube part, which is relatively great, acts upon the rear side of the valve flap and pulls it up firmly against the tubing opening. Therefore, for lifting the valve flap, the surgeon needs not only the force to overcome the resistance of the elastic, flexible support, but additionally, the vacuum prevailing on the rear side of the valve flap must be overcome so that, with actuation of the valve flap, this latter must forcefully be guided, with a "jolt", into the open position. This has operational disadvantages. In many cases, it is not desirable to always have the full vacuum available at the suctioning opening of the aspirator, rather, in certain cases of application, it is very well worth striving for that only a minimal suction force be capable of being set at the end of the suctioning tube, whereby the variation of this suctioning force should not result from valve type arrangements in the vacuum line, rather being capable of being adjusted manually by the operator in the particular case of application at hand. In other words: in the case of the known apparatus according to DE-AS 29 50 323, fine-setting by the operator himself can be carried out only with difficulty.

Generally, in the case of an aspirator of the precedingly described species, needing to be taken into account during the time in which the aspirator is not used and the suction line is closed to the outside, is that the vacuum produced by the vacuum machine inside the suction line be capable of building up in full scope, so that following some period of quiescent time of the aspirator, there prevails on the rear side of the valve flap a vacuum in the magnitude of approximately 0.8 atm. By intake of air during operation of the aspirator, normally available at the suctioning opening is a vacuum of only 0.3 atm. Hence, in the case of known aspirators, the full vacuum is effective immediately upon opening the valve which, in the case of many operations, is extremely undesirable since aspirating capacity is too great.

Finally, in the case of the aspirator according to DE-AS 29 50 323, the space in which the valve flap is acting is not accessible, i.e. corrections of a false position of the valve flap are possible only with very great difficulty. Because of the cast link connection, no positive guidance of the valve flap is guaranteed. Additionally formed, under the tubing section of the suctioning tube projecting into the valve space, is a space in which dirt particles and uncontrollable secretion residues and bone splinters can collect, which under some circumstances, can lead to faulty operation of the valve flap.

Likewise, described in U.S. Pat. No. 4,212,300 is an operation aspirator that is considered in the apparatus first above described. In the case of this known arrangement, described is a valve stem that is capable of moving against the resetting force of an elastic tension (pulling) means, said stem displaying a pass through opening that can be brought into alignment or out of alignment with the pass through opening in the housing of the actuating mechanism of the aspirator, so that opening or closing of the aspirator is therewith possible. Here, the closure process likewise results because of the elastic reset means for the valve stem, automatically upon releasing the aspirator. In the case of this known arrangement also, it is very difficult to set a fine-metering of the vacuum at the suctioning opening since, in order to achieve an absolute sealing of the valve stem in the closure position, this latter (stem) must be guided in relatively aspiration-sealed fashion inside the boring accommodating the valve stem. With actuation of the valve stem, this frictional resistance must be overcome, additionally the reset force of the elastic reset means, so that a fine-adjustment of the valve stem is not achievable with this arrangement either. Additionally, upon opening the valve, the full vacuum is active, which in many cases of operation is extremely undesirable, since aspirating capacity is too great.

SUMMARY OF THE INVENTION

The task underlying the invention is to obtain an operation aspirator in which the valve mechanism is accessible as easily as possible and that can be operated one-handed so that, in this manner, the hand of the operator is unencumbered when actuating the aspirator and, additionally, a fine-metering at the suctioning opening is possible, whereby, nevertheless, a collection of secretion residues and bone splinters in the region of the valve flap is avoided.

This task underlying the invention is resolved by the characterizing portion of the principal claim and by the characterizing portion of claim 10.

The principal claim proposes an arrangement wherein the two sections of suctioning tubing, at least in the top region, are joined via an elastic means that supports actuation of the valve flap, at least in the initial phase, i.e. therefore, the first opening movement of the valve flap must occur only against the vacuum acting upon the rear side of the valve flap, with this opening force that is required being supported by an auxiliary force incorporated in the elastic wall. It is only when a partial opening of the valve flap has occurred, hence when the full vacuum is no longer active against the rear side of the valve flap, that the opening movement needs to be carried out further against the elastic force of the housing wall. This provides the operator with the possibility, already in the initial phase of opening movement, to execute partial opening of the flap, so that a fine-metering at the aspirator tip is forcefully achieved.

Proposed in the case of the form of solution according to claim 10 is that a false air opening be provided that is inactive in the closure positioning of the valve stem closing off the suction line, but becoming partially active when guiding the valve stem into an aligning position with the suctioning line, so that, thereby, the action of the vacuum is not fully conducted to the aspirator tip, the vacuum action being rather partially removed by aspiration via the false air opening, during which time then, when the valve stem is in the fully open position, the false air opening is closed by a section of the valve stem so that, now, the full vacuum is available at the aspirator tip and even heavy blood clots, bone particles and the like can be suctioned out there. The atmospheric-side opening of the false air hole is thereby protected against contaminations by contacts.

Advantageous forms of embodiment of the invention are explained in the subclaims.

BRIEF DESCRIPTION OF THE DRAWINGS

Described in the following description are two forms of embodiment of the invention. Shown are.

DETAILED DESCRIPTION OF THE INVENTION

Figure 1:
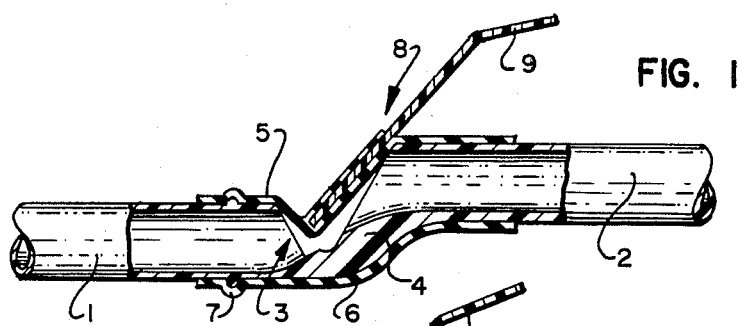
FIG. 1 is a first form of embodiment of the invention wherein the valve flap is in the quiescent position, i.e. no vacuum is active against the rear side of the valve flap.
Figure 2:
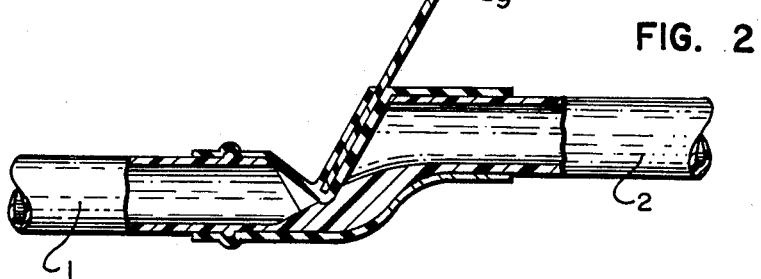
FIG. 2 is the form of embodiment according to FIG. 1 with vacuum acting on the rear side.
Figure 3:
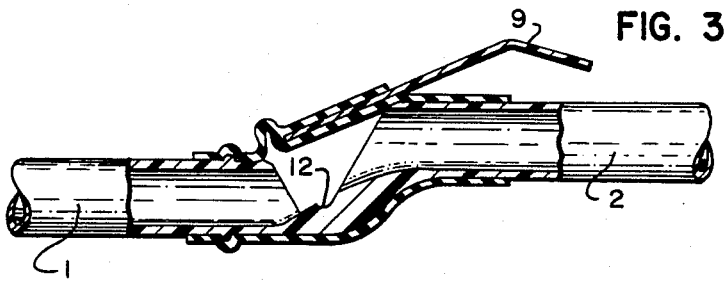
FIG. 3 is the form of embodiment according to FIG. 1 with fully opened valve flap.

Represented in FIGS. 1 to 3 are two pieces of tubing 1 and 2 that form the actual aspirating (suctioning) tube, with the opening, i.e. the aspirator head, not being illustrated in the drawing. The two pieces of tubing 1 and 2 are offset to one another in step fashion and display, at least on their top side, a cutout 3. Here, the tubes can be produced in one piece in a single manufacturing process such that this cutout is provided, with the floor sides of the tubes then being formed by a thickening 4 constructed one-piece with the tubing pieces 1 and 2.

Both pieces of tubing 1 and 2 are joined with one another by a housing 5 that consists of a piece of rubber hose 6 and, as an example, can be attached, by means of appropriate shapings 7 or auxiliary tubing clamps, to the pieces of tubing 1 and 2.

At the top side of the housing illustrated, i.e. the area lying in the region of the cutout 3, there is provided an insertion pocket 8 into which is placed, in the case of the example of embodiment illustrated, an operating lever 9. Naturally, the operating lever 9 can also be formed out one-piece from the piece of rubber hose 6 or cast one-piece therein.

The operating lever 9 can consist of metal and be replaceable, and in the same fashion can be produced from plastic, so that when disposing of waste, disassembly of the operating lever is not required.

In place of the insertion pocket illustrated and the structure of the top side of the housing illustrated, this can be constructed, in the region where the valve flap is to be formed, as a spherical body or a partially spherical body. Also capable of being provided for in place of the operating lever 9 is that there be arranged on this spherical body a tension element (pull-element) so that operation of the valve occurs not by a pressure action, but rather by an influencing pull.

Shaping, selection of materials and, therewith, the elastic reset capability of the piece of rubber hose 6 is such that, in the quiescent condition, i.e. with the vacuum not effective in the pieces of tubing 1 and 2, the valve flap formed by that part of the operating lever located in the insertion pocket 8 is in a position in which this flap does not close the opening of the piece of tubing 2, rather, in this quiescent position, the opening in tubing 2 is partially open, i.e. not closed by the valve flap.

Instead of the thickening 4 being formed out one-piece from the two tubing pieces 1 and 2, it is naturally also possible to provide the thickening 4 in the piece of rubber hose 6 and to install the pieces of tubing 1 and 2 as separate components.

Now, if a vacuum is generated in the piece of tubing 2, the valve flap closes because of the suctioning force acting on the rear side of the valve flap, i.e. it closes the opening of the piece of tubing 2.

For opening the valve flap, as is made clear in FIG. 3, the operating lever 9 is pushed down until it raises the elastic rubber housing above the cutout 3, so that there is therewith obtained a free flowthrough opening for the vacuum.

Capable of being seen from a comparison of illustrations 1 to 3 is that, for opening the valve flap from the position illustrated in FIG. 2 into the position illustrated in FIG. 3, first needing to be overcome is the suctioning force of the vacuum prevailing in the piece of tubing 2, whereby the elasticity of the housing contributes to overcoming this suctioning force, namely the housing itself is indeed constrained to lift the operating lever into the position illustrated in FIG. 1.

Figure 4:
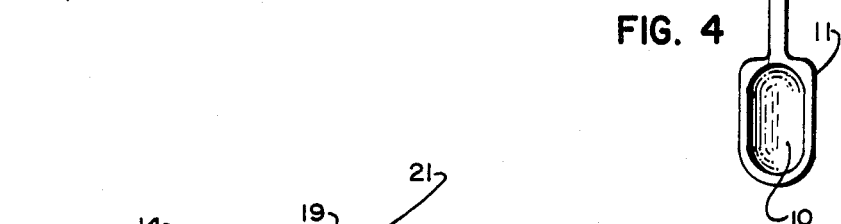
FIG. 4 shows, in a top view, the actuation stem that is capable of being installed in the elastic wall.

The operating lever is illustrated in FIG. 4, and capable of being recognized is that the part 10 of the operating lever that is capable of being inserted in the insertion pocket 8 is constructed in arched fashion and displays a planar outer edge 11, with the arching being spherical section-shaped, but extended longitudinally and, therefore, oval, so that there is therewith enabled an as large as possible free flowthrough cross section in the suctioning position of the operating lever illustrated in FIG. 3. The operating lever can, however, also be embodied pinform so that, in this fashion, when it is raised, the desired distortion of the housing results automatically.

Capable of being recognized at 12 is a circular depression in the thickened part 4, into which the lower part of the plane outer edge 11 of the operating lever 9 places itself. FIG. 2 shows this closure position.

Figure 5:
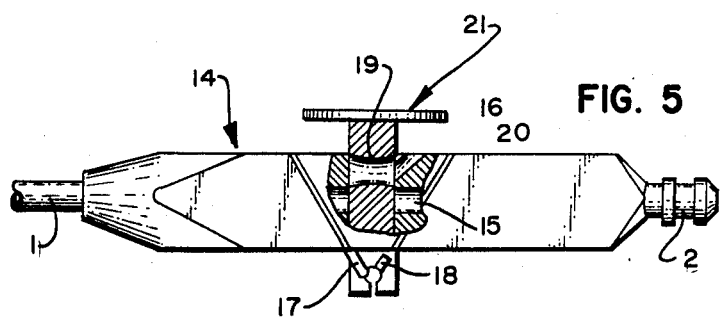
FIG. 5 is a modified form of embodiment that is equipped with a movable valve stem that is perpendicular to the suctioning line.

In the illustration in FIG. 5, provided is an actuating grip 14 into which open out the two tubing ends 1 and 2 and that is equipped with a passthrough boring 15. Disposed perpendicularly to the boring 15 is a valve stem 16 that is movable against the action of elastic reset means 17 and 18. Illustrated in FIG. 5 is the closure position of the aspirator, i.e. boring 19 running through inside the valve stem 16 does not align with boring 15 in the operating part 14, so that the vacuum still prevailing in the piece of tubing 2 is interrupted and does not reach the aspirator tip. Illustrated at 20 is a false air boring opening out into the boring 19, which is ineffective in the position illustrated in FIG. 5. The actuating disc 21 is selected large enough so that it projects over the false air boring 20, such that the opening of the false air boring 20 cannot be utilized with the finger of the operating person. Now, if the valve stem 16 is moved downwardly, after a short interval of travel boring 19 comes into alignment with boring 15, but the false air boring 20 also comes into communication with boring 15 via boring 19, so that, in this fashion, there results, in the first motion of the opening movement, a considerable reduction of the vacuum at the end of the aspirator itself. It is only when the valve stem is fully guided into the position in which boring 15 aligns with boring 19 that the false air boring 20 is brought into an ineffective position, and the full vacuum prevails at the aspirator opening. Here, by shaping the opening of the false air boring 20 toward the valve stem 16, it is possible to further support this effect, for example if this opening is constructed to be oval, triangular or the like, i.e. if the opening of the false air boring 20 toward the valve passthrough 19—as seen in the direction of opening movement of the valve stem 16—is constructed in tapering fashion.

The position and size of boring 15, 19 and 20 can also be selected such that, at the beginning of actuation of the disc 21, only false air is sucked in, so that a very delicately sensitive control is possible.

Naturally, also capable of being provided in place of the piece of rubber hose 6 illustrated in FIG. 1 to 3 is a jacket-like piece of rubber or piece of plastic that can be placed about both of the pieces of tubing 1 and 2, and closed.

What is claimed is:

1. A manual medical surgical aspiration device for the aspiration of body fluids consisting of two pieces of tubing at least one of which terminates in a diagonal face relative to its longitudinal axis forming a seat which are joined by an elastic tubing which forms a housing, said tubing having a flexible cutout pocket means having inner wall means which extend within said housing, a flap member means extending within said pocket means acts as a interruption member to control the level of vacuum in the device, an operating lever extending from the flap member exteriorly of said housing and directly connected to said flap member means to control the flap member means to force said inner wall means against said diagonal face such that in a quiescent condition said valve flap member means does not completely close off said diagonal face of said tubing, said housing further consisting of a single unitary piece of elastic tubing opposite said pocket means the ends of which are laterally offset to one another along the longitudinal axis.

2. An aspirator according to claim 1, wherein the housing (5), bridging over the two pieces of tubing, consists of a piece of rubber hose (6) on which is provided, formed out on its upper side, the insertion pocket (8).

3. An aspirator according to claim 1, wherein the housing (5) consists of a jacket, consisting of an elastic rubber material and capable of being closed about the two pieces of tubing (1,2).

4. An aspirator according to claim 1, wherein the operating lever (9), in its area located inside the pocket (8), is constructed in spherical section-form (at 10) with an upwardly arched spherical surface and displays a plane outer edge (11).

5. An aspirator according to claim 1, wherein the operating lever (9) consists of plastic.

6. An aspirator according to claim 1, wherein the operating lever is only constructed pin-fashion.

7. An aspirator according to claim 1, wherein the operating lever is constructed as a tension (pull) element on the top side of the housing part forming the valve flap.

* * * * *